United States Patent [19]

Fuchs et al.

[11] Patent Number: 4,931,592
[45] Date of Patent: Jun. 5, 1990

[54] STORABILITY OF MOLTEN CYCLOHEXANONE OXIME

[75] Inventors: Hugo Fuchs, Ludwigshafen; David Agab, Rimbach; Gerald Neubauer, Weinheim; Josef Ritz, Ludwigshafen, all of Fed. Rep. of Germany

[73] Assignee: BASF Aktiengesellschaft, Ludwigshafen, Fed. Rep. of Germany

[21] Appl. No.: 429,799

[22] Filed: Oct. 31, 1989

[30] Foreign Application Priority Data

Nov. 23, 1988 [DE] Fed. Rep. of Germany ....... 3839448

[51] Int. Cl.$^5$ ............................................. C07C 131/04
[52] U.S. Cl. ...................................... 564/267; 564/264
[58] Field of Search ................................ 564/267, 264

[56] References Cited

U.S. PATENT DOCUMENTS

| | | | |
|---|---|---|---|
| 3,941,838 | 3/1976 | Fuchs et al. | 564/267 |
| 4,031,139 | 6/1977 | Rapp et al. | 564/267 |
| 4,256,668 | 3/1981 | Mathew et al. | 564/267 |
| 4,281,194 | 7/1981 | Armor et al. | 564/267 |

*Primary Examiner*—James H. Reamer
*Attorney, Agent, or Firm*—Keil & Weinkauf

[57] ABSTRACT

The storability of molten cyclohexanone oxime containing 0.5–15% by weight of cyclohexanone and 1–8% by weight of aqueous ammonium bisulfate solution is improved by washing the molten cyclohexanone oxime with a 10–42% strength by weight aqueous ammonium sulfate solution and maintaining a pH of 4.5–5.8.

7 Claims, No Drawings

STORABILITY OF MOLTEN CYCLOHEXANONE OXIME

The product after preparing cyclohexanone oxime by reacting cyclohexanone with an aqueous hydroxylammonium/ammonium sulfate solution at above the melting point of cyclohexanone oxime in the absence of solvents or buffer salts at a low pH, as described in U.S. Pat. No. 4,031,139, is a cyclohexanone oxime which besides small amounts of unconverted cyclohexanone contains an aqueous solution of ammonium bisulfate of pH<2.0. Since it is frequently not possible to use the cyclohexanone oxime at the rate at which it is produced, it is necessary to store it until required. But it has been found that cyclohexanone oxime which has been stored for a relatively short period before being used to prepare caprolactam no longer produces the requisite UV and permanganate numbers.

U.S. Pat. No. 3,941,838 discloses that a cyclohexanone oxime obtained by oximation of cyclohexanone with hydroxylammonium salt solutions and neutralization with ammonia is subsequently treated with concentrated ammonium sulfate solution at pH 3-6 or hydroxylammonium salt solutions in order to reduce the water content. There is no mention of how a cyclohexanone oxime prepared by another method might be improved in storability.

It is an object of the present invention to improve the storability of molten cyclohexanone oxime obtained by acid oximation, to reduce the formation of cyclohexenone during storage, and to avoid the difficulties which arise on using stored cyclohexanone oxime in the preparation of caprolactam.

We have found that this object is achieved by a process for improving the storability of a molten cyclohexanone oxime which contains from 0.5 to 15% by weight of cyclohexanone and from 1 to 8% by weight of aqueous ammonium bisulfate solution by washing the molten cyclohexanone oxime with a 10-42% strength by weight aqueous ammonium sulfate solution and maintaining a pH of 4.5-5.8.

The novel process has the advantage that cyclohexanone oxime obtained from acid oximation can be stored safely for at least one day without adverse consequences in the further processing into caprolactam. The novel process has the further advantage that formation of cyclohexenone is suppressed even if the cyclohexanone content is comparatively high.

The starting compound used is a molten cyclohexanone oxime which contains 0.5-15% by weight, in particular 0.5-2% by weight, of cyclohexanone and 1-8, in particular 4-8%, by weight of aqueous ammonium bisulfate solution. The aqueous ammonium bisulfate solution present in the molten cyclohexanone oxime generally contains from 0.01 to 0.5% by weight of ammonium bisulfate and has a pH of <2.0, for example of from 0.5 to 1.5. A suitable melt of cyclohexanone oxime is obtained for example by reacting cyclohexanone and aqueous hydroxylammonium/ammonium sulfate solution at above the melting point of cyclohexanone oxime in the absence of solvents, neutralizing agents and/or buffer salts until equilibrium is attained. Advantageously, the reaction is carried out in countercurrent. A suitable method is described for example in U.S. Pat. No. 4,031,139.

The cyclohexanone oxime to be treated is advantageously at from 70° to 95° C., in particular at from 70° to 85° C.

According to the present invention, the molten cyclohexanone oxime is washed with a 10-42% strength by weight aqueous ammonium sulfate solution while a pH of 4.5 to 5.8 is maintained. The pH is particularly advantageously 5.2-5.8. It is also advantageous to use a 15-35% strength by weight aqueous ammonium sulfate solution.

It is advantageous to use per part by volume of cyclohexanone oxime from 0.1 to 10, in particular from 0.5 to 5 parts, by volume of aqueous ammonium sulfate solution of the concentration mentioned.

It is possible to carry out the wash in batchwise fashion in a stirred vessel in which the pH is maintained by the addition of aqueous ammonia solution. Advantageously, the cyclohexanone oxime is washed repeatedly, for example up to 5 times. Again advantageously, the wash is carried out continuously by charging a column from the bottom with molten cyclohexanone oxime and from the top, in countercurrent, with aqueous ammonium sulfate solution. To ensure thorough mixing, suitable apparatus comprises for example rotary disk columns, mixer settlers and packed columns. It is advantageous to charge the column in the course of the wash with aqueous ammonia solution at the rate required to maintain the specified pH.

Cyclohexanone oxime is suitable for preparing caprolactam.

The process according to the present invention may be illustrated with reference to the following Examples:

EXAMPLE 1

A cyclohexanone oxime containing 10% by weight of cyclohexanone in equilibrium with a 20% strength by weight aqueous ammonium bisulfate solution was washed 5 times at 80° C. with the same amount (by volume) of a 23% strength by weight aqueous ammonium sulfate solution at pH 5.5. The color of the cyclohexanone oxime thus treated and the level of impurities were monitored at 90° C. over 75 hours. The treated cyclohexanone oxime only became discolored after 24 hours. After 75 hours, the level of cyclohexen-2-one was 30 ppm and the concentration of UV-active impurities was 230 ppm in total.

COMPARATIVE EXAMPLE 1

Untreated cyclohexanone oxime of the type used in Example 1 shows a slight yellow color after as short a time as 4 hours at 90° C., and the level of UV-active impurities was 230 ppm and that of cyclohexen-2-one 30 ppm.

EXAMPLE 2

Example 1 is repeated, except that 40% strength by weight aqueous ammonium sulfate solution at pH 5.5 is used. The treated oxime only became discolored at 90° C. after 24 hours. After 50 hours, the concentration of UV-active compounds was 200 ppm and the level of cyclohexen-2-one was 21 ppm.

We claim:

1. A process for improving the storability of a molten cyclohexanone oxime containing from 0.5 to 15% by weight of cyclohexanone and from 1 to 8% by weight of aqueous ammonium bisulfate solution by washing the molten cyclohexanone oxime with a 10-42% strength by weight aqueous ammonium sulfate solution and maintaining a pH of 4.5–5.8.

2. A process as claimed in claim 1, wherein the pH is set by the addition of aqueous ammonia solution.

3. A process as claimed in claim 1, wherein a pH of 5.2–5.8 is maintained.

4. A process as claimed in claim 1, wherein 15–35% strength by weight aqueous ammonium sulfate solution is used.

5. A process as claimed in claim 1, wherein 75°–90° C. is maintained.

6. A process as claimed in claim 1, wherein per part by volume of cyclohexanone oxime from 0.1 to 10 parts by volume of aqueous ammonium sulfate solution are used.

7. A process as claimed in claim 1, wherein the cyclohexanone oxime is continuously introduced at the bottom end of a wash column an aqueous ammonium sulfate solution is passed downward through the column, and cyclohexanone oxime is removed at the top end of the column and aqueous ammonium sulfate solution at the bottom end.

* * * * *